United States Patent [19]

Cook et al.

[11] Patent Number: 4,908,441

[45] Date of Patent: Mar. 13, 1990

[54] DEOXYADENOSINE COMPOUNDS AND METHODS OF MAKING AND USING THE SAME

[75] Inventors: Phillip D. Cook, Downingtown, Pa.; Dennis J. McNamara, Ann Arbor, Mich.

[73] Assignee: Warner-Lambert Company, Morris Plains, N.J.

[21] Appl. No.: 221,478

[22] Filed: Jul. 19, 1988

[51] Int. Cl.$^4$ .................. C07H 19/173; C07H 19/20
[52] U.S. Cl. ........................................ 536/27; 536/28; 536/29
[58] Field of Search ............... 536/27, 28, 29; 514/46, 514/47

[56] References Cited

PUBLICATIONS

D. A. Carson, D. Bruce Wasson, and Ernest Beutler, Proc. Natl. Acad. Sci. U.S.A. vol. 81; pp. 2232–2236, 1984.

Christenson et al, J. Med. Chem, vol. 15(7), pp. 736–739, 1972.

Carson et al.(I), Blood, vol. 62(4), pp. 737–743, 1983.

Carson et al(II), Proc. Nat. Acad Sci. U.S.A., vol. 77(11), pp. 6865–6869, 1980.

Carson et al(IV), Proc. Nat. Acad. Sci. U.S.A., vol. 79, pp. 3848–3852, 1982.

*Primary Examiner*—Ronald W. Griffin
*Assistant Examiner*—L. Eric Crane
*Attorney, Agent, or Firm*—Ronald A. Daignault

[57] ABSTRACT

3'-Acyl-2-chloro-2'-deoxy-5'-adenylic acids (I) as well as a method for their production, pharmaceutical compositions comprising the compounds, and methods of treatment using the compound in dosage forms. The compounds of the invention have pharmacological properties and are useful antimicrobial agents and antitumor agents.

4 Claims, No Drawings

DEOXYADENOSINE COMPOUNDS AND METHODS OF MAKING AND USING THE SAME

TECHNICAL FIELD

The invention relates to novel 3'-acyl-2-chloro-2'-deoxy-5'-adenylic acids, to methods for their production, to pharmaceutical compositions comprising the compounds, and to use of the compounds and methods of treatment using the compounds in dosage form. The compounds of the invention have pharmacological properties and are useful antimicrobial agents and antitumor agents.

BACKGROUND OF THE INVENTION

The deoxynucleoside, 2-chloro-2'-deoxyadenosine, is known (D. A. Carson, D. Bruce Wasson, and Ernest Beutler, Proc. Soc. Acad. Sci. USA, Vol. 81, pp 2232–2236, 1984) for its antileukemic and immunosuppressive activity both in mammals and in Phase 1 clinical trial in patients.

SUMMARY OF THE INVENTION

The invention in one aspect relates to novel compounds, having the structural formula I

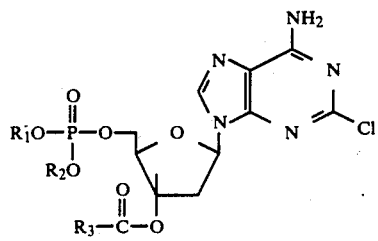

where $R_1$ and $R_2$ each independently represent H, $NH_4$, an alkali metal, or $C_1$ to $C_8$ alkylamine, or together represent an alkaline earth metal, and $R_3$ is a $C_1$ to $C_8$ alkyl group. Preferred compounds are 2-chloro-2'-deoxy-5'-adenylic acid, 3'-acetate, and the sodium, potassium, lithium, ammonium, n-butylamine, n-octylamine, and triethylamine mono and disalts. Also preferred are the calcium, magnesium, and barium monosalts. Whereas the known nucleoside 2-chloro-2'-deoxyadenosine is sparingly soluble in water, e.g., ca. 1 mg/ml as a feature of the present invention, the present compounds have surprisingly enhanced water solubility, e.g., >100 mg/ml. Thus, the invention allows for formulation of the present nucleotide to be administered in clinically acceptable dosage forms which the known nucleoside did not provide.

The invention in another aspect includes a method for preparing 3'-acyl-2-chloro-2'-deoxy-5'-adenylic acids having the above formula I, which comprises reacting 3'-acyl-2-chloro-2'-deoxyadenosine with a phosphorylating agent and isolating the resulting 3'-acyl-2-chloro-2'-deoxy-5'-adenylic compound in free acid form or salt form. In carrying out the reaction, one uses a suitable medium such as trimethylphosphate and a phosphorylating agent such as phosphoryl chloride. The reaction is carried out in the cold and is usually complete within three to five hours. For the isolation of the product in a preferred procedure, the reaction mixture is combined with ice water containing sodium bicarbonate sufficient for neutralization. The reaction mixture, after ether extraction, concentration, and ethanol precipitation of solids, is further processed as an aqueous filtrate by silica gel column chromatography to obtain a high yield of product, containing sodium chloride. The sodium chloride is then removed using a polystyrene resin. It is found that the product obtained in the preferred isolation procedure using silica gel chromatography is the monosodium salt. In another preferred isolation procedure for the production of the disodium salt product, one uses column chromatography with a suitable resin, preferably with a polystyrene resin having a high porosity rating such as HP20, HP21, or SP207 resin to obtain high purity chloride-free product.

In an alternative procedure, the phosphorylation reaction mixture is neutralized in ice water saturated with ammonia, and the resulting ammonium disalt phosphate product is recovered in a manner analogous to the above isolation procedure. In still another procedure, the free 3'-acyl-2-chloro-2'-deoxy-5'-adenylic acid is obtained by subjecting the monosodium salt or disodium salt product to ion exchange with a suitable exchange material in the acid form. To convert the metal ion to a different ion for purposes of isolating the product, ion-exchange chromatography is suitably employed preferably using a given alkali metal salt column, alkaline earth metal salt column or alkylamine salt column respectively of, for example, a sulfonic acid cation-exchanged resin.

In still another preferred procedure, a given mono- or disalt of the free acid having the structural formula I is obtained by neutralizing the free acid in an aqueous solvent with an equivalent amount of a water soluble salt forming compound and removing the solvent.

The invention in one composition aspect relates to a pharmaceutical composition for treating microbial infection comprising an antimicrobially effective amount of a compound having formula I and a pharmaceutically acceptable carrier.

The invention in another composition aspect relates to a pharmaceutical composition for inhibiting the growth of leukemic cells in experimental animals exemplified by rodents such as the mouse, comprising a cell growth inhibiting amount of a compound having the above formula I and a pharmaceutically acceptable carrier.

The invention in another composition aspect relates to a pharmaceutical composition for inhibiting the growth of solid tumor cells in experimental animals exemplified by rodents such as the mouse, comprising a cell growth inhibiting amount of a compound having the above formula I and a pharmaceutically acceptable carrier.

The invention in another aspect relates to a method for treating microbial infection which comprises administering an antimicrobially effective amount of a compound having formula I to an animal in need thereof.

The invention in another method aspect relates to a method for inhibiting the growth of leukemic cells which comprises administering a leukemic cell growth inhibiting amount of a compound having formula I to an animal in need thereof.

The invention in another method aspect relates to a method for inhibiting the growth of solid tumor cells which comprises administering a solid tumor cell growth inhibiting amount of a compound having formula I to an animal in need thereof.

DETAILED DESCRIPTION

The compounds of the present invention are prepared overall from the known 2-chloro-2'-deoxyadenosine as illustrated by the following reaction scheme:

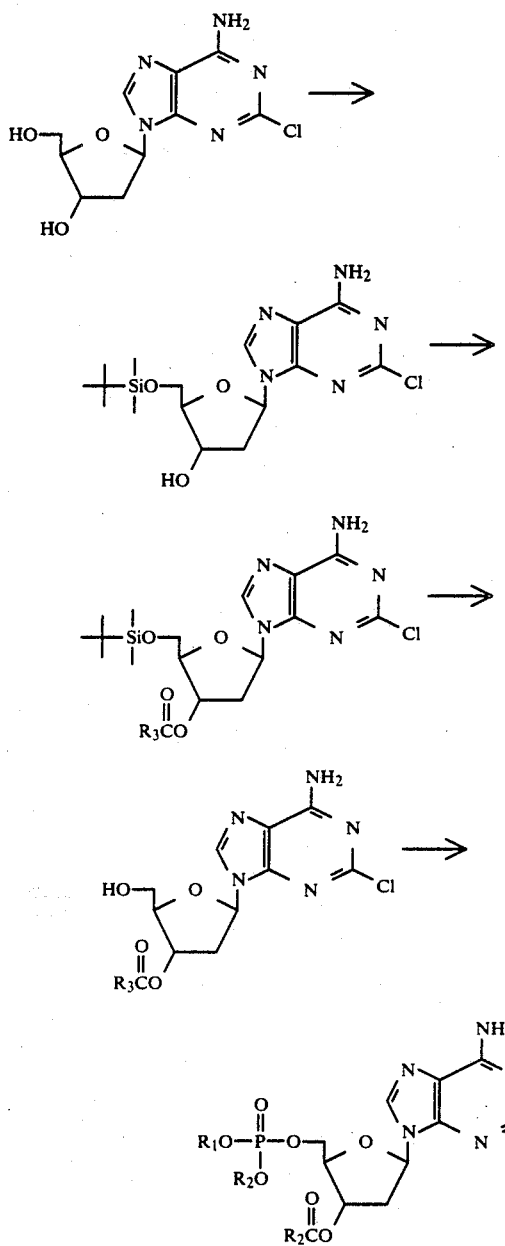

2-Chloro-2'-deoxyadenosine is treated with a silyl halide, preferably a trialkylsilylhalide, e.g., t-butyldimethylsilyl chloride, in an inert solvent, e.g., dimethylformamide, and in the presence of an activating agent, e.g., imidazole, to provide the 5'-silylether, which is acylated with the appropriate acid anhydride in the presence of pyridine solvent and optionally in the presence of a catalyst, e.g., 4-dimethylaminopyridine, to afford the 3'-acyl-2-chloro-2'-deoxyadenosine,5'-silylether. The silyl blocking group is then removed by known methods, e.g., with tetrabutylammonium fluoride, in an inert solvent, e.g., an ether such as tetrahydrofuran. The corresponding 3'-acyl-2-chloro-2'-deoxyadenosine is phosphorylated as already described above.

PHYSICAL AND PHARMACOLOGICAL PROPERTIES OF THE COMPOUNDS

The compounds of the invention are useful as pharmacological agents, as indicated, for the treatment of microbial infection, and for the treatment of leukemia and solid tumors in experimental, warm-blooded animals exemplified by rodents such as the mouse. The activity of representative compounds of the invention was established by test protocols described below.

One test protocol is the in vitro antibacterial/antifungal (ABF) test. Compounds are tested for antimicrobial activity in an agar-disk diffusion assay, a standard microbiological technique for testing antibiotics. After incubation of each culture with a test compound, a zone of inhibition is determined. By this test, the present compounds typically are cidal against gram-negative bacterial species (*Escherichia coli* 04863) and gram-positive bacteria (*Bacillus subtilis* 04555, and *Streptococcus faecalis* 05045) at concentrations in the range from 500 to 1000 micrograms/ml.

Another test protocol is the in vivo assay for antileukemic activity. This assay is carried out with male $CD_2F_1$ mice (six per treatment group) that weigh 22–24 grams at first treatment. L1210 leukemia cells are harvested from the peritoneal ascites fluid of a leukemic male $DBA_2$ mouse and diluted with sterile 0.9% saline containing 2.1% W/V bovine serum albumin, 2000 U/ml penicillin, and 0.3 mg/ml streptomycin. The cells are counted with a Coulter counter. The mice are randomized, inoculated with $10^4$ L1210 cells (0.5 ml, IP), and rerandomized to treatment or control groups on Day 0. The test compound is dissolved in 10% aqueous dimethylsulfoxide. Treatment groups are injected IP with 0.5 ml of freshly made DMSO solutions of the test compound once daily on Days 3–7. Control mice are treated with 0.5 ml 10% dimethylsulfoxide. All mice are weighed on Days 3 and 7 and all dying mice are autopsied to confirm the presence of advanced leukemia. A % T/C value [T/C computed as (median lifespan of the treated group/median lifespan of the control group)] greater than 125 is considered as showing significant activity. The results for nucleotide compounds and compositions of the invention exemplified by 3'-acetyl-2-chloro-2'-deoxy-5'-adenylic acid, monosodium salt, are presented in Table I.

TABLE I

Antitumor Activity 3'-acetyl-2-chloro-2'-deoxy-5'-adenylic acid Monosodium Salt
(Example 1, infra)

| Dose mg/kg | % T/C Animals (1) | (2) |
|---|---|---|
| 200 | Tx* | |
| 124 | Tx, | 87 |
| 77 | 126, | 112 |
| 48 | 124, | 149 |
| 42 | | 183 |
| 31 | | 149 |
| 25 | | 160 |
| 16 | | 149 |

*Tx = Toxic

A test protocol to show activity of the compounds of the present invention against solid tumors was that described below, for example, in inhibiting the growth of colon tumors.

The tumor growth delay assay assesses the antitumor activity of a test agent by measurement of the treatment-induced delay of tumor growth.

Tumor Inoculum

Test animals were $CD2F_1$ hybrid mice derived from the inbred strain of tumor origin. After the required mice were randomized they received 30–50 mg subcutaneous implants of either colon 36 or colon 8 by trocar on Day 0. Samples of each donor tumor were incubated in thioglycolate media as a check for contamination of the tumor material. After tumor inoculation mice were rerandomized and distributed at 10 mice per treatment group (20 for control).

Treatment

Drug treatment was initiated when tumors reached measurement in two dimensions by the formula:

$$\text{tumor weight (mg)} = (a+b^2)$$

where a and b are the tumor length and width, respectively. Drug, suspended in methyl-cellulose, was administered intraperitoneally Q4HX3 for nine consecutive days in a range of toxic to nontoxic doses. Tumor-bearing control groups were injected with methyl-cellulose. Animal survival was monitored daily. Tumors were measured twice weekly and animal weights recorded on a weekly basis. All dead mice were autopsied to determine the cause of death (drug or tumor). Any mouse bearing a tumor larger than the smallest lethal control tumor for two consecutive measurements was sacrificed, provided that greater than 25 days had elapsed since last treatment. Any tumor-free mouse was retained long enough so that a single surviving tumor cell at last treatment could grow to an unmistakable subcutaneous tumor.

Calculations

T/C was calculated based on the difference in days required for the treated (T) and control (C) groups to reach an evaluation size of 1000 mg. Gross and net logs of cell kill were determined based on standard methodologies. The degree of activity or rating is a function of cell kill. Activity is defined in accordance with the standard methodologies as follows:

| | |
|---|---|
| Toxic | Tx |
| High Activity | ++++ |
| Marked Activity | +++ |
| Moderate Activity | ++ |
| Slight Activity | + |
| Inactive | − |
| Unsatisfactory Test | UT |

The results for nucleotide compounds and compositions of the invention exemplified by 3'-acetyl-2-chloro-2'-deoxy-5'-adenylic acid, monosodium salt, are presented in Table II.

TABLE II

| | Antitumor Activity 3'-Acetyl-2-chloro-2'-deoxy-5'-adenylic Acid, Monosodium Salt (Example 2, infra) | | | |
|---|---|---|---|---|
| Tumor | Dose* mg/kg | T/C | Net Kill | Rating |
| Colon 08 | 15 | 12.9 | 0.4 | + |
| Colon 36 | 9.5 | 14.0 | 0.6 | ++ |

*Dose at which greatest activity is seen.

PREPARATION OF PHARMACEUTICAL COMPOSITIONS

When used as a pharmacological agent or pharmaceutical composition, the compounds of the composition aspect of the invention can be prepared and administered in any of a wide variety of topical, oral, and parenteral dosage forms.

For preparing pharmaceutical compositions, one uses an inert, pharmaceutically acceptable carrier which carrier can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the compound is mixed with carrier having the necessary binding properties in suitable proportion and compacted in the shape and size desired. The powders and tablets preferably contain from 5 or 20 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desire. Aqueous suspensions suitable for oral use can be made by dispersing the finely divided active component in water with viscous material, e.g., natural or synthetic gums, resins, methyl cellulose, sodium carboxymethyl cellulose, and other suspending agents.

Topical preparations include dusting powders, creams, lotions, gels, and sprays. These various topical preparations may be formulated by well known procedures. See for example Remington's Pharmaceutical Sciences, Chapter 43, 14th Ed., Mack Publishing Co., Easton, Pennsylvania 16042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as pharmacological agents, the compound utilized in the pharmaceutical method of this invention is administered at the initial dosage of about 0.1 mg to about 50 mg per kilogram. A dose range of about 0.5 mg to about 10 mg per kilogram is preferred. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compound may also be administered parenterally or intraperitoneally. Solutions of the compound can be prepared in water mixed if desired with a surfactant such as hydroxypropylcellulose. Dispersions can also be prepared in glycerol, liquid polyethylene glycols, and mixtures thereof, and in oils. Under ordinary conditions of storage and use these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various 30 antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredients into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the compound is generally present in from about 0.1 to about 500 mg/ml of carrier. In the case of compositions containing supplementary active ingredients, the dosages are determined by reference to the usual dose and the manner of administration of the said ingredients. The daily parenteral doses range from 0.1 mg/kg to 10 mg/kg. The preferred daily dose range is 0.3 mg/kg to 10 mg/kg. The preferred daily dose range is 0.3 mg/kg to 10 mg/kg.

The invention and the best mode of practicing the same are illustrated by the following examples. In the examples temperatures are given in degrees Celsius.

EXAMPLE

2-Chloro-2'-deoxy-5'-adenylic Acid, 3'-acetate, Monosodium Salt, Monohydrate

A.

2-Chloro-2'-deoxy-5'-O-[(1,1-dimethylethyl)dimethylsilyl]-adenosine.

To a solution of 7.43 g (0.026 m) of 2-chloro-2'-deoxyadenosine in 150 mL of DMF, cooled by an ice-bath, was added 3.94 g (0.0578 m) of imidazole followed by 4.31 g (0.0286 m) of t-butyldimethylsilyl chloride. The solution was stirred cold 1.5 hours, then for 2 hours with the ice-bath removed. To the cooled solution was added another 0.79 g (0.012 m) of imidazole followed by 0.86 g (0.0057 m) of t-butyldimethylsilyl chloride. The solution was stirred for 1 hour, then treated with 150 mL of MeOH. The solution was concentrated at 50° C. at oil pump pressure. The resulting residue was partitioned between $H_2O$ and EtOAc. The EtOAc layer was dried ($MgSO_4$) and concentrated to give 10.94 g of a solid. This material was dissolved in $CH_3OH/CH_2Cl_2$ and the solution was treated with 75 g of flash silica gel. The solvents were evaporated and the powder was applied to a column of 900 g of flash silica gel packed in $CH_2Cl_2$/MeOH (100:1). Elution was initially performed using $CH_2Cl_2$/MeOH (100:1), then 50:1, then 20:1. Appropriate fractions were pooled and concentrated to give 8.74 g (84.0%) of the product as a white solid. This material had the same tlc characteristics as a previously, similarly synthesized and characterized sample, and was itself not further characterized (tlc: $SiO_2$ (CH$_2$Cl$_2$/MeOH, 20:1, Rf≃0.3. The physical characteristics of the previously characterized sample follow: mp 195°–196° C., with resolidification at 198° C.

Anal. for C$_{16}$H$_{26}$N$_5$O$_3$ClSi: Calcd.: C, 48.05; H, 6.55; N, 17.51; Cl, 8.86. Found: C, 48.17; H, 6.31; N, 17.60, Cl, 8.77.

IR (KBr)γ=2930, 2859, 1643, 1594, 1314, 838 cm$^{-1}$.

NMR (DMSO, 100 MHz)δ=0.0 (s, 6, Si(CH$_3$s)$_2$), 0.8 (s, 9, C(CH$_3$)$_3$), 4.4 (m, 1, H-3'), 6.3 (t, J=6.5 Hz, 1, H-1'), 7.8 (s, 2, NH$_2$), 8.3 (s, 1, H-8).

B
2-Chloro-2'-deoxy-5'-O-[(1,1-dimethylethyl)dimethylsilyl]-adenosine, 3'-acetate.

To a solution of 1.15 g (0.00288 m) of 2-chloro-2'-deoxy-5'-O-[(1,1-dimethylethyl)dimethylsilyl]-adenosine in 20 mL of dry pyridine, cooled by an ice-bath, was added a catalytic amount of 4-dimethylaminopyridine, followed by 0.45 mL (0.00047 m) of acetic anhydride. The ice-bath was removed and the solution was stirred at room temperature for 4 hours. A small amount of ice was added to the solution and it was concentrated at reduced pressure, coevaporating with PhCH$_3$ and EtOH. The resulting solid was dissolved in EtOAc, and the solution was washed twice with H$_2$O, dried (MgSO$_4$), and concentrated to give 1.3 g (100%) of the product as a white solid. This material had the same tlc characteristics as a previously, similarly synthesized and characterized sample, and was itself not further characterized (tlc: SiO$_2$(CH$_2$Cl$_2$:MeOH, 10:1, R$_f$≃0.7). The physical characteristics of the previously characterized sample follow: mp 134°–135° C.

Anal. for C$_{18}$H$_{28}$N$_5$O$_4$ClSi: Calc.: C, 48.91; H, 6.39; N, 15.84; Cl, 8.02. Found: C, 49.36; H, 6.24; N, 15.73; Cl, 7.79.

IR (KBr)γ=2932, 2859, 1744, 1648, 1595, 1311, 1241 cm$^{-1}$.

NMR (DMSO, 200 MHz)δ=0.0 (s, 6, Si(CH$_3$)$_2$), 0.8 (s, 9, C(CH$_3$)$_3$);,

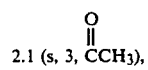

2.1 (s, 3, ÖCCH$_3$), 2.5 (m, 1, H-2'), 2.9 (m, 1, H-2'), 3.8 (m, 2, H-5'), 4.1 (m, 1, H-4'), 5.3 (m, 1, H-3'), 6.3 (t, 1, H-1'), 7.8 (s, 2, NH$_2$), 8.3 (s, 1, H-8).

C. 2-Chloro-2'-deoxyadenoxine, 3'-acetate.

To a solution of 10.36 g (0.0234 m) of 2-chloro-2'-deoxy-5'-O-[(1,1-dimethylethyl)dimethylsilyl]-adenosine, 3'-acetate, in 100 mL of THF, cooled in an ice-bath, was added 46.9 mL (0.0469 m) of a 1.0 M solution of tetrabutylammonium fluoride in THF. The ice-bath was removed and the solution was stirred for 18 hours at room temperature. The solution was concentrated and the residue was coevaporatd with PhCH$_3$. To the residue was added MeOH, and the solid which formed was collected. Recrystallization from EtOH gave 5.53 g (73.3%) of the product as an off-white solid. This material was combined with material from another experiment to give one lot of material, mp 186°–188° C. with resolidification to give material which does not melt <250° C.

Anal. for C$_{12}$H$_{14}$ClN$_5$O$_4$: Calcd.: C, 43.98; H, 4.31; N, 21.37. Found: C, 43.81; H, 4.27; N, 21.43.

NMR (DMSO, 200 MHz), δ=2.06 (s, 3, CH$_3$), 2.5 (m, 1, 2'-H), 2.8 (m, 1, 2'-H), 3.60 (m, 2, 5'-H), 4.06 (m, 1), 5.14 (t, J =5.7 Hz, 1, 5'-OH, disappears on D$_2$O addition), 5.32 (d, J =5.6 Hz, 1), 6.25 (dd, J =5.89 Hz, 8.55 Hz, 1, 1'-H), 7.86 (s, 2, NH$_2$, disappears on D$_2$O addition), 8.38 (s, 1, 8-H).

MS (DEI): m/e =327 (M$^+$).

IR (KBr)γ=2869, 1744, 1673, 1608, 1578, 1315, 1233 cm$^{-1}$.

D 2-Chloro-2'-deoxy-5'-adenylic Acid, 3'-acetate, Monosodium Salt, Monohydrate.

To a solution of 11.4 g (0.0348 m) of 2-chloro-2'-deoxyadenosine, 3'-acetate (dried at 80° C. at oil pump pressure over P$_2$O$_5$ for 18 hours) in 100 mL of 95% triethylphosphate, cooled by an ice-bath, was added dropwise 4.99 mL (0.0535 m) of phosphoryl chloride during 30 minutes. The solution was stored at 0° C. for 18 hours. This cold solution was added to a cold solution of 22.7 g (0.27 m) of NaHCO$_3$ in 300 mL of distilled H$_2$O. This solution was allowed to stand at 0° C. for 2 hours, and was then extracted with ether. To the H$_2$O layer was added 100 g of flash silica gel. The suspension was concentrated at 40° C. at oil pump pressure to give a powder which was triturated in ether. The resulting powder was applied to a column of 700 g of flash silica gel packed in CH$_3$CN:H$_2$O (4/1) and eluted with the same solvent. The appropriate fractions were pooled, filtered, and concentrated to give 17.2 g of a white solid.

Two liters of Sepabeads (Mitsubishi), a polystyrene resin, were placed in a column and washed with H$_2$O. To this column was applied a solution of 16.5 g of the above solid dissolved in a minimum amount of H$_2$O. Elution with H$_2$O removed the NaCl as evidenced by a AgNO$_3$ test. Then gradually increasing amounts of MeOH were added to the eluant until the eluant was 100% MeOH. Appropriate fractions were pooled, concentrated at 40° C. at oil pump pressure, and coevaporated with EtOH to give 6.9 g (46%) of material. Drying at room temperature at oil pump pressure over P$_2$O$_5$ or 18 hours gave the product as a white solid, mp 170°–173° C.

Anal. for C$_{12}$H$_{14}$ClN$_5$O$_7$PNa.H$_2$O: Calc.: C, 32.19; H, 3.60; N, 15.64; Cl, 7.92; Na, 5.14, H$_2$O, 4.02; P, 6.92. Found: C, 32.22, H, 3.68; N, 15.75; Cl, 8.03; Na, 5.41; H$_2$O, 4.35; P, 6.79.

IR (KBr)γ=1735, 1654, 1599, 1357, 1316, 1249 cm$^{-1}$.

HPLC (Altex C-18), 98.5%.

[α]$_D^{22}$ −23.1° (cl.26, H$_2$O).

NMR (DMSO, 100 MHz)δ=2.07 (s, 3, CH$_3$), 5.40 (m, 1, 3'-H), 6.27 (distorted q, 1, 1'-H, peak width 13.4 Hz), 7.93 (br s, 2, NH$_2$, disappears upon D$_2$O addition), 8.67 (s, 1, H-8).

I claim:
1. A compound having the structural formula

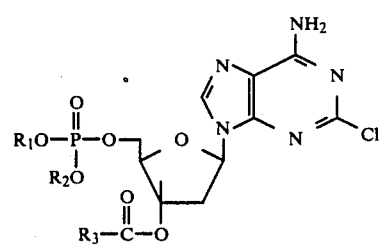

where R$_1$ and R$_2$ each independently represent H, NH$_4$, an alkali metal or a C$_1$ to C$_8$ alkylamine or together represent an alkaline earth metal, and $R^3$ is a $C_1$ to $C_8$ alkyl group.

2. A compound according to claim 1 which is the free acid 2-chloro-2'-deoxy-5'-adenylic acid, 3'-acetate.

3. A compound according to claim 1 which is 2-chloro-2'-deoxy-5'-adenylic acid, 3'-acetate, sodium salt.

4. A compound according to claim 3 which is the monosodium salt.

* * * * *